US011981720B2

(12) United States Patent
Shen

(10) Patent No.: US 11,981,720 B2
(45) Date of Patent: May 14, 2024

(54) USE NOVEL LIGHT SENSITIVE CHANNEL PROTEIN VR 1.0 IN PREPARATION OF RETINAL PHOTORECEPTOR CELL DEGENERATIVE DISEASE DRUG

(71) Applicant: ZHONGMOU THERAPEUTICS CO., LTD., Hubei (CN)

(72) Inventor: Yin Shen, Hubei (CN)

(73) Assignee: ZHONGMOU THERAPEUTICS CO., LTD., Hubei (CN)

(*) Notice: Subject to any disclaimer, the term of this patent is extended or adjusted under 35 U.S.C. 154(b) by 0 days.

(21) Appl. No.: 18/120,007

(22) Filed: Mar. 10, 2023

(65) Prior Publication Data

US 2023/0348552 A1 Nov. 2, 2023

Related U.S. Application Data

(63) Continuation of application No. PCT/CN2022/097893, filed on Jun. 9, 2022.

(30) Foreign Application Priority Data

Apr. 12, 2021 (CN) ......................... 202110388643.8

(51) Int. Cl.

| | |
|---|---|
| ***A61P 27/02*** | (2006.01) |
| ***C07K 14/705*** | (2006.01) |
| ***C12N 15/86*** | (2006.01) |
| *A61K 38/00* | (2006.01) |
| *A61K 48/00* | (2006.01) |

(52) U.S. Cl.

CPC ............ *C07K 14/705* (2013.01); *A61P 27/02* (2018.01); *C12N 15/86* (2013.01); *A61K 38/00* (2013.01); *A61K 48/00* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 2013/0066047 | A1 | 3/2013 | Spudich et al. |
| 2013/0066402 | A1 | 3/2013 | Lin et al. |
| 2015/0232528 | A1 | 8/2015 | Spudich et al. |
| 2017/0339930 | A1 | 11/2017 | Lee et al. |
| 2018/0305417 | A1 | 10/2018 | Spudich et al. |

FOREIGN PATENT DOCUMENTS

| | | |
|---|---|---|
| CN | 110023327 | 7/2019 |
| CN | 112010952 | 12/2020 |
| CN | 112011554 | 12/2020 |
| CN | 113173984 | 7/2021 |
| WO | 2018/044912 | 3/2018 |

OTHER PUBLICATIONS

International Search Report dated Sep. 16, 2022, in International (PCT) Application No. PCT/CN2022/097893, with English translation.

Hiroshi Tomita et al., "Channelrhodopsin-2 gene transduced into retinal ganglion cells restores functional vision in genetically blind rats", Experimental Eye Research, vol. 90, No. 3, 2009, pp. 429-436.

Xiao-min Wang et al., "Application and outlook of channelrhodopsin-2 in system neuroscience", Chinese Bulletin of Life Sciences, vol. 29, No. 8, 2017, pp. 797-803, with English Abstract.

Kejiong Shen et al., "New advances in gene therapy with adenoviral vectors for inherited retinal diseases", Chin J Ocul Fundus Dis, vol. 36, No. 3, Mar. 2020, pp. 242-248, with English Abstract.

Oleg A. Sineshchekov et al., "Intramolecular Proton Transfer in Channelrhodopsins", Biophysical Journal, vol. 104, 2013, pp. 807-817.

Hiroshi Tomita et al., "Restoration of Visual Response in Aged Dystrophic RCS Rats Using AAV-Mediated Channelopsin-2 Gene Transfer", Investigative Ophthalmology & Visual Science, vol. 48, No. 8, 2007, pp. 3821-3826.

GenBank DataBase, channelopsin [*Tetraselmis subcordiformis*]; Accession No. AGF84747.1; GenBank DataBase; Feb. 20, 2013.

EMBL, UniprotKB-M1PFK4 (M1PFK4_TETSU); Accession No. M1PFK4; EMBL; May 1, 2013.

*Primary Examiner* — Neil P Hammell
*Assistant Examiner* — Khaleda B Hasan
(74) *Attorney, Agent, or Firm* — Wenderoth, Lind & Ponack, L.L.P.

(57) ABSTRACT

Disclosed is a use of a novel light sensitive channel protein VR 1.0 in the preparation of a retinal photoreceptor cell degenerative disease drug, belonging to the field of biomedicine. The amino acid sequence of the present light sensitive channel protein VR 1.0 is shown in SEQ ID NO. 1, and the nucleotide sequence of the encoding gene thereof is shown in SEQ ID NO. 2. The present light sensitive channel protein VR 1.0 maintains a stable current signal under a high frequency response while having high sensitivity and fast dynamics, and also has a faster response frequency under same light stimulation conditions. The present protein has clear therapeutic effects on retinal photoreceptor cell degenerative diseases, and can be used to prepare a drug for restoring the photoreceptor function in the retina, restoring the vision or photosensitive ability of a subject, and treating retinal degenerative diseases. In the present application, a new idea for developing photogenetic therapy for retinal photosensitive cell degenerative diseases is provided, and options for clinical optogenetic therapy are expanded.

5 Claims, 3 Drawing Sheets

Specification includes a Sequence Listing.

SEQ ID NO: 2, encoding gene sequence of *VR1.0*

```
atgcgacccc aaatactcct cttgctggct ttgttgaccc ttggactggc taacggaaca    60
gaaggtccca acttctacgt tcctttcagc aataagacag gcgtagtcag atccatgggc   120
ttccagctca atccggaata cctgaacgaa acaattttgc tggacgactg tacgccaatc   180
tatctgaacg tcggtcccct gtgggagcaa aaggttgccc gaggtacgca atggtttggt   240
gttatcctct cgttggcgtt tctcatctat tatatatgga taacatataa ggcgacttgc   300
ggatgggaag aactgtacgt gtgtacgatc gaattttgta aaattgtaat tgaactctac   360
ttcgagtttt cgcctccggc gatgatatat cagaccaacg gagaggtaac gccctggttg   420
cgatatgctg aatggctctt gacctgccca gtcatttgca tacatttgag taacattaca   480
ggactcaatg acgactattc gggccgaact atgtccctga tcacatccga cctgggaggc   540
atctgcatgg ccgttacttc cgccttgagt aaaggctggt tgaagtggct ctttttcgtg   600
atcggctgtt gttacggtgc tagtacgttt tatcatgcgg cgctcatata tatagaaagt   660
tactacacta tgcctcacgg tgtttgtaaa aacatggtat tggcgatggc agcggtattt   720
tttacaagtt ggttcatgtt tcccggtttg ttcctggcag gccctgaagg aaccaatgca   780
ctgtcgtggg cgggctcgac tatcggtcat accgtggcag atttgctctc caaaaacgcc   840
tggggtatga ttggtcactt cctccgactg gagatacaca aacatataat tattcatggt   900
gatgttcgtc gcccgataac ggttaatacc ttgggacgag aagtcacggt gtcgtgtttt   960
gtcgataaag aagaggagga tgaagacgaa cgtatcagca ctaagaccta cgcgaaccgg  1020
gca                                                                1023
```

Fig. 1

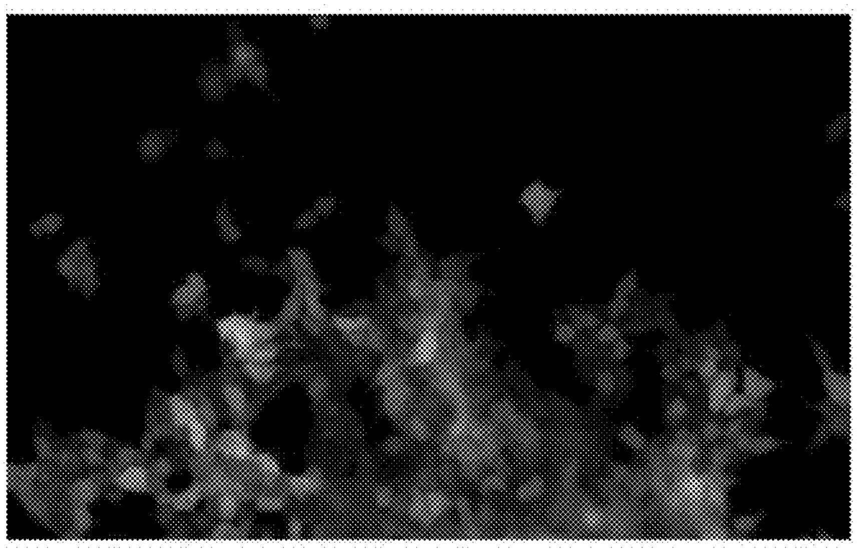

Fig. 2

USE NOVEL LIGHT SENSITIVE CHANNEL PROTEIN VR 1.0 IN PREPARATION OF RETINAL PHOTORECEPTOR CELL DEGENERATIVE DISEASE DRUG

CROSS REFERENCES TO RELATED APPLICATIONS

This application claims priority of Chinese patent application CN202110388643.8 filed on Apr. 12, 2021, the contents of which are incorporated herein by reference in its entirety.

REFERENCE TO AN ELECTRONIC SEQUENCE LISTING

The contents of the electronic sequence listing (Attach-B_Sequence_listing-0038A.xml; Size: 5,036 bytes; and Date of Creation: Jul. 24, 2023) is herein incorporated by reference in its entirety.

TECHNICAL FIELD

The application belongs to the field of biomedicine, and particularly relates to use of a novel light-sensitive channel protein VR1.0 in the preparation of a medicament for treating a retinal photoreceptor cell degenerative disease.

BACKGROUND ART

Retinal photoreceptor cell degenerative diseases are a group of degenerative diseases characterized by progressive loss of photoreceptor cell and pigment epithelial function. Such diseases are mainly caused by genetic mutations or retinal pigment epithelial (RPE) cell dysfunction. Common typical examples are retinitis pigmentosa (RP) and age-related macular degeneration (AMD), which are also two important and troublesome eye diseases leading to blindness. The prevalence of degeneration of photoreceptor cells caused by genetic causes is about 1/3500-1/4000. There are currently 400,000 patients with retinitis pigmentosa in China, and more than 1.5 million patients worldwide. The secondary retinal photoreceptor cell degenerative diseases caused by acquired drugs and disease causes are also increasing day by day.

Due to the irreversible apoptosis of photoreceptor cells in retinal photoreceptor cell degenerative diseases, and the high genetic heterogeneity of the most diseases, the treatment of related diseases has become very difficult. Current treatment means include stem cell transplantation, gene therapy, retinal prosthesis implantation, and optogenetics, etc. Optogenetics utilizes the integrity of the remaining structure of the degenerative retina, and uses adeno-associated virus (AAV) as a vector to achieve targeted expression of light-sensitive proteins in the cone cells (early degeneration), ON-type bipolar cells or ganglion cells (middle and late stages of degeneration), so as to restore the light response of the retina. In addition, stem cells, virtual reality systems and holographic imaging technologies can be combined to restore visual function.

Optogenetics, as a therapeutic strategy that does not rely on the gene function of the mutation site and can respond to light stimulation at the single-cell level, has great potential in the treatment of retinal photoreceptor cell degenerative diseases. However, the biological performance of optogenetic tools has been a key factor limiting the recovery of visual function, especially photosensitivity and kinetics. The photosensitive proteins currently used for visual restoration do not balance photosensitivity and kinetics well to meet visual signal demands. Therefore, there is a need for a medicament for treating a retinal photoreceptor cell degenerative disease, which has both high sensitivity and fast kinetics, and maintains the stability of the current signal under high-frequency response.

SUMMARY OF THE APPLICATION

The object of the present application is to overcome the shortcomings and deficiencies of the prior art, and provides a novel light-sensitive channel protein VR1.0 having both high sensitivity and fast kinetics, and use of the light-sensitive channel protein VR1.0 in the preparation of a medicament for treating a retinal photoreceptor cell degenerative disease.

The object of the present application is achieved through the following technical solutions:

A light-sensitive channel protein VR1.0, with a total of 341 amino acids, has an amino acid sequence represented by the following SEQ ID NO: 1:

```
MRPQILLLLALLTLGLANGTEGPNFYVPFSNKTGVVRSMGFQLNPEYLNE
TILLDDCTPIYLNVGPLWEQKVARGTQWFGVILSLAFLIYYIWITYKATC
GWEELYVCTIEFCKIVIELYFEFSPPAMIYQTNGEVTPWLRYAEWLLTCP
VICIHLSNITGLNDDYSGRTMSLITSDLGGICMAVTSALSKGWLKWLFFV
IGCCYGASTFYHAALIYIESYYTMPHGVCKNMVLAMAAVFFTSWFMFPGL
FLAGPEGTNALSWAGSTIGHTVADLLSKNAWGMIGHFLRLEIHKHIIIHG
DVRRPITVNTLGREVTVSCFVDKEEEDEDERISTKTYANRA
```

An encoding gene of the above light-sensitive channel protein VR1.0, with a total of 1023 nucleotides, has a nucleotide sequence represented by the following SEQ ID NO: 2:

```
atgcgacccc aaatactcct cttgctggct ttgttgaccc ttggactggc taacggaaca    60
gaaggtccca acttctacgt tcctttcagc aataagacag gcgtagtcag atccatgggc   120
ttccagctca atccggaata cctgaacgaa acaattttgc tggacgactg tacgccaatc   180
tatctgaacg tcggtcccct gtgggagcaa aaggttgccc gaggtacgca atggtttggt   240
gttatcctct cgttggcgtt tctcatctat tatatatgga taacatataa ggcgacttgc   300
ggatgggaag aactgtacgt gtgtacgatc gaattttgta aaattgtaat tgaactctac   360
ttcgagtttt cgcctccggc gatgatatat cagaccaacg gagaggtaac gccctggttg   420
```

-continued

```
cgatatgctg aatggctctt gacctgccca gtcatttgca tacatttgag taacattaca    480
ggactcaatg acgactattc gggccgaact atgtccctga tcacatccga cctgggaggc    540
atctgcatgg ccgttacttc cgccttgagt aaaggctggt tgaagtggct ctttttcgtg    600
atcggctgtt gttacggtgc tagtacgttt tatcatgcgg cgctcatata tatagaaagt    660
tactacacta tgcctcacgg tgtttgtaaa aacatggtat tggcgatggc agcggtattt    720
tttacaagtt ggttcatgtt tcccggtttg ttcctggcag gccctgaagg aaccaatgca    780
ctgtcgtggg cgggctcgac tatcggtcat accgtggcag atttgctctc caaaaacgcc    840
tggggtatga ttggtcactt cctccgactg gagatacaca aacatataat tattcatggt    900
gatgttcgtc gcccgataac ggttaatacc ttgggacgag aagtcacggt gtcgtgtttt    960
gtcgataaag aagaggagga tgaagacgaa cgtatcagca ctaagaccta cgcgaaccgg   1020
gca                                                                 1023
```

A vector comprising the encoding gene of the above light-sensitive channel protein VR1.0, wherein it can express the above light-sensitive channel protein VR1.0 after being transferred into a host cell.

A recombinant virus comprises the encoding gene of the above light-sensitive channel protein VR1.0 or a vector comprising the encoding gene, and the recombinant virus can express the above light-sensitive channel protein VR1.0 after being transferred into a host cell. The recombinant virus may be a recombinant adeno-associated virus.

Use of the above light-sensitive channel protein VR1.0, and the encoding gene, vector or recombinant virus of the light-sensitive channel protein VR1.0 in the preparation of a medicament, wherein the medicament includes a medicament for restoring the function of photoreceptors in the retina, a medicament for restoring the vision, a medicament for restoring photosensitive ability, a medicament for treating a retinal degenerative disease.

A medicament comprising the above light-sensitive channel protein VR1.0, the encoding gene, vector or recombinant virus of the light-sensitive channel protein VR1.0, wherein the medicament includes a medicament for restoring the function of photoreceptors in the retina, a medicament for restoring the vision, a medicament for restoring photosensitive ability, a medicament for treating a retinal degenerative disease.

Advantages and beneficial effects of the present application: the present application confirms that light-sensitive channel protein VR1.0 has a significant therapeutic effect in the treatment of retinal photoreceptor cell degenerative diseases. The novel light-sensitive channel protein maintains a stable current signal under a high frequency response while having high sensitivity and fast dynamics, and also has a faster response frequency under same light stimulation conditions. The present application provides a new idea for developing optogenetic therapy for retinal photosensitive cell degenerative diseases, expands options for clinical optogenetic therapy, and has great application and promotion value.

BRIEF DESCRIPTION OF THE DRAWINGS

FIG. 1 is the encoding gene sequence of VR1.0.

FIG. 2 is a fluorescence image of HEK 293T cells transfected with adeno-associated virus rAAV2/2-CMV-VR1.0-EGFP carrying VR1.0 sequence for 48 hours.

FIG. 3A: the current diagram generated by stimulating VR1.0 for is under the conditions of 470 nm wavelength and light intensity of $2.7\times10^{16}$ $8.2\times10^{15}$, $6.4\times10^{14}$, and $7.9\times10^{13}$ photons/$cm^2$ s; FIG. 3B: the magnitude of the current recorded under the experimental conditions in FIG. 3A; FIG. 3C: the current response of VR1.0 under the condition of 470 nm wavelength and light intensity of $2.7\times10^{16}$ photons/$cm^2$ s, with the light stimulation frequency of 2, 4, 8, 16 and 32 Hz; wherein "photons/$cm^2$ s" is the light intensity unit.

FIG. 4A: images of retinal sections of rd1 mice treated with rAAV2/2-CMV-VR1.0-EGFP under a fluorescence microscope; FIG. 4B: the current diagram of RGCs expressing VR1.0-EGFP recorded by whole-cell mode patch-clamp.

FIG. 5A: representative oscillogram of visual evoked potentials for C57BL/6J, rd1 mice treated with intravitreal injection of rAAV2/2-CMV-VR1.0-EGFP, and rd1 littermate mice without any treatment; FIG. 5B: statistical histogram of visual evoked potential N1 amplitude for the above three groups of mice; wherein $P<0.001$, there is a significant difference.

FIG. 6A: schematic pattern of the experiments in a light/dark box; FIG. 6B: statistical histogram of the activity time of the above three groups of mice in a light box; wherein $P<0.05$, there is a significant difference.

DETAILED DESCRIPTION OF THE APPLICATION

The following examples are used to further illustrate the present application, but should not be construed as limiting the present application. Unless otherwise specified, the technical means used in the Examples are conventional means well known to those skilled in the art.

Example 1: Packaging of rAAV2/2-CMV-VR1.0-EGFP Recombinant Virus

VR1.0 gene fragment with BamHI and KpnI restriction sites added at both ends was synthesized, and the restriction endonucleases BamHI and KpnI were used to respectively digest the VR1.0 gene fragment and the viral vector (GV388, pAAV-CMV bGlobin-MCS-eGFG-3Flag), then recovering and ligating; the ligation product was used to transform Trans5α chemically competent cells. The colony transferred with the recombinant plasmid was screened, and after expanding culture, the plasmid was extracted for sequencing verification. The sequence results are shown in FIG. 1, indicating that the recombinant plasmid GV388-VR1.0 was successfully constructed. AAV helper-free system was used to produce recombinant adeno-associated virus. AAV helper-free system was mainly composed of viral vector (GV388), pAAV-RC vector and pHelper vector (purchased from Shanghai Jikai Gene Chemical Technology Co., Ltd.), performed virus packaging with reference to the AAV helper-free system instructions to obtain rAAV2/2-CMV-VR1.0-EGFP recombinant adeno-associated virus (the virus serotype is rAAV type 2, i.e., rAAV2/2; the promoter is cytomegalovirus (CMV) sequence, and the marker gene is EGFP).

Example 2: Culture of Cell Line HEK 293T and Transfection of rAAV2/2-CMV-VR1.0-EGFP Virus HEK 293T cells were firstly inoculated in 5 mL medium containing 10% fetal bovine serum, 1×DMEM (Dulbecco's Modified Eagle Medium), 100 U/mL penicillin G and 100 μg streptomycin in a 6 cm petri dish, then performing subculture in a biochemical incubator at 37° C., 95% air, and 5% $CO_2$. After the HEK 293T cells covering about 90% of the petri dish, the HEK 293T cells were transferred to a 24-well plate including gelatin-coated glass slides for culture, and the medium is the same as above; after culturing for 24 h, the cells were transfected with rAAV2/2-CMV-VR1.0-EGFP virus. The serum in the 24-well plate was aspirated out with a negative pressure suction tube to replace with 1 mL medium containing 1% fetal bovine serum, 1×DMEM, 100 U/mL penicillin G and 100 μg streptomycin, then adding 2 μL rAAV2/2-CMV-VR1.0-EGFP virus (a titer of 1.01 E+12 vg/mL) to culture continuously for 48 h. After the culture was completed, the expression was observed with a fluorescence microscope. The results are shown in FIG. 2, rAAV2/2-CMV-VR1.0-EGFP virus can be highly expressed on HEK 293T cells.

Example 3: Responses to Light Recorded by Whole-Cell Mode Patch-Clamp

Figure 3:
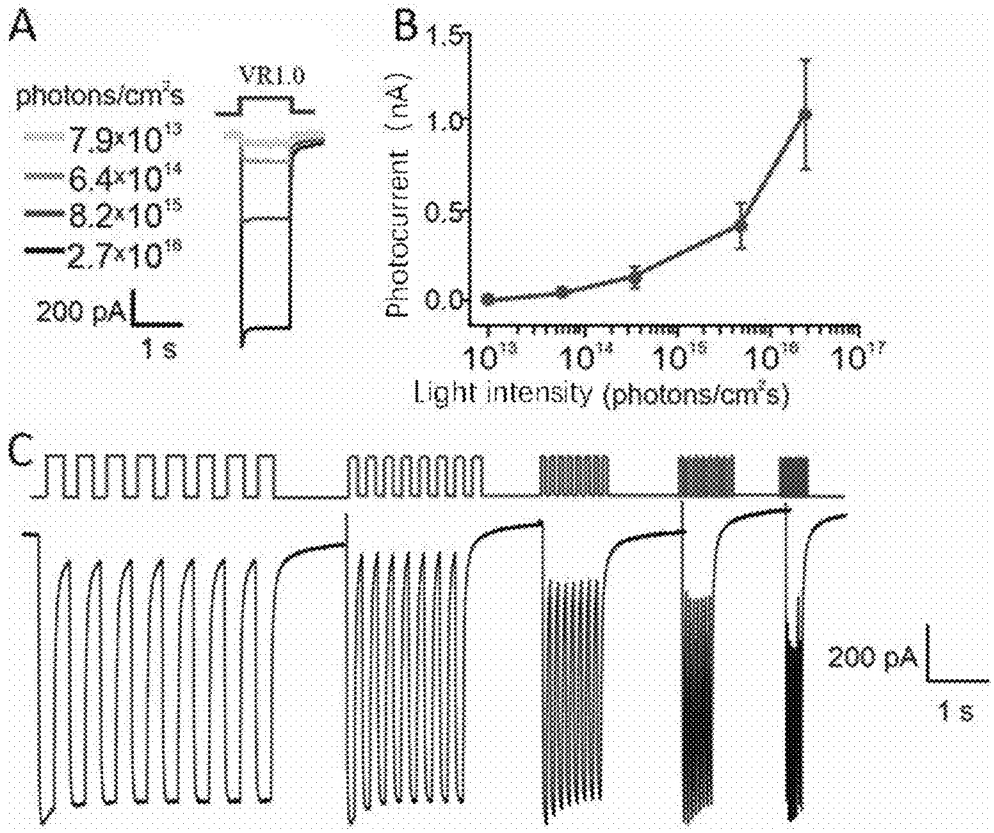
FIG. 3 is the photocurrent recorded by patch-clamp after expressing VR1.0 in HEK 293T cells, reflecting the photosensitivity (A, B) and response frequency (C) of VR1.0.

After culturing the transfected HEK 293T cells for 48 h, the cells were recorded by whole-cell mode patch-clamp at a constant room temperature of 25° C. Extracellular fluid: 140 mmol/L sodium chloride, 5 mmol/L potassium chloride, 2 mmol/L calcium chloride, 20 mmol/L 4-hydroxyethylpiperazine ethane sulfonic acid, 16 mmol/L glucose, adjusting the pH with sodium hydroxide to 7.4 and placing at room temperature; intracellular fluid: 115 mmol/L cesium methanesulfonate, 20 mmol/L cesium chloride, 2.5 mmol/L magnesium chloride, 0.6 mmol/L ethylene glycol bis(2-aminoethyl ether)tetraacetic acid, 10 mmol/L 4-hydroxyethylpiperazine ethane sulfonic acid, 4 mmol/L adenosine 5'-triphosphate magnesium salt, 0.4 mmol/L guanosine 5'-triphosphate sodium salt, 10 mmol/L phosphocreatine, adjusting pH with cesium hydroxide to 7.2 and keeping on ice. 30 min before the experiment, the extracellular fluid was pre-oxygenated with 100% $O_2$. A glass microelectrode (BF150-86-10, Sutter Instrument) was drawn with a horizontal puller (signal MODEL P-1000, Sutter Instrument Company), and the resistance was 6-8 MΩ HEK 293T cells transfected with rAAV2/2-CMV-VR1.0-EGFP virus were placed in the extracellular fluid for dark adaptation for 30 min, and the patch-clamp experiment was performed after the cells were stabilized. In order to verify the photosensitivity of VR1.0, the current was recorded under the light intensity of $2.7\times10^{16}$, $8.2\times10^{15}$, $6.4\times10^{14}$, and $7.9\times10^{13}$ photons/cm$^2$ s, and the VR1.0 was allowed to fully recover after 1 s light stimulation under the light intensity of $2.7\times10^{16}$ photons/cm$^2$ s; the open time constant and close time constant were analyzed by Clampfit 10.6 software. In addition, in order to explore the response frequency of VR1.0 to light, pulse light stimulation of 2, 4, 8, 16 and 32 Hz was set. The light source is Mightex external optical fiber (470 nm), the stimulation time is set by BioLED control software, and the specific light intensity is measured by an optical power meter. The results are shown in FIG. 3, particularly, FIG. 3A is the current diagram generated by stimulating VR1.0 for 1 s under the conditions of 470 nm wavelength and light intensity of $2.7\times10^{16}$, $8.2\times10^{15}$, $6.4\times10^{14}$, and $7.9\times10^{13}$ photons/cm$^2$ s; FIG. 3B is the magnitude of the current recorded under the experimental conditions in FIG. 3A; FIG. 3C is the current response of VR1.0 under the conditions of 470 nm wavelength and light intensity of $2.7\times10^{16}$ photons/cm$^2$ s, with the light stimulation frequency of 2, 4, 8, 16 and 32 Hz. According to the guidelines of International Commission on Non-Ionizing Radiation Protection (ICIRP), the safe light intensity of 470 nm blue light on the retina should not exceed $7.62\times10^{14}$ photons/cm$^2$ s, and VR1.0 can generate photocurrent under the condition of $7.9\times10^{13}$ photons/cm$^2$ s which is far lower than the retinal safe light intensity threshold, and will not cause phototoxicity to the retina. Secondly, in terms of response frequency, 24 Hz is needed for visual signal processing, and VR1.0 can respond to light stimulation of at least 32 Hz to meet the visual signal requirements.

Example 4: Intravitreal Injection of Virus rAAV2/2-CMV-VR1.0-EGFP in Rd1 Mice 4-week-old rd1 mice were anesthetized by intraperitoneal injection of a mixture of 100 mg/kg ketamine and 12 mg/kg xylazine according to body weight. After adequate anesthesia, the ocular surface and periorbital skin were disinfected with 0.5% povidone iodine. In order to reduce the discomfort caused by intravitreal injection to the mice, the eyeballs of the mice were topically anesthetized with proparacaine hydrochloride eye drops (alcaine). The mouse was fixed to expose the eyeball, and a Nanoject III high-precision microinjector (Drummond Scientific, USA) with a glass microelectrode (WPI, USA) was used to suck 1.5 μL of rAAV2/2-CMV-VR1.0-EGFP virus (a titer of 1.01 E+12 v.g/mL), the intravitreal injection was completed by inserting a needle 0.5 mm below the corneoscleral limbus on the nasal side of the mouse, and the intravitreal injection of the other eye was completed in the same way. After the injection, levofloxacin hydrochloride ophthalmic gel (Jackie) was applied on the eyeballs of the mice to prevent infection. Two weeks later, a needle was inserted at 0.5 mm below the corneoscleral limbus on the temporal side of the mouse in the same manner, to perform a second virus injection with the same virus dose. The curative effect was observed after one month.

Figure 4:
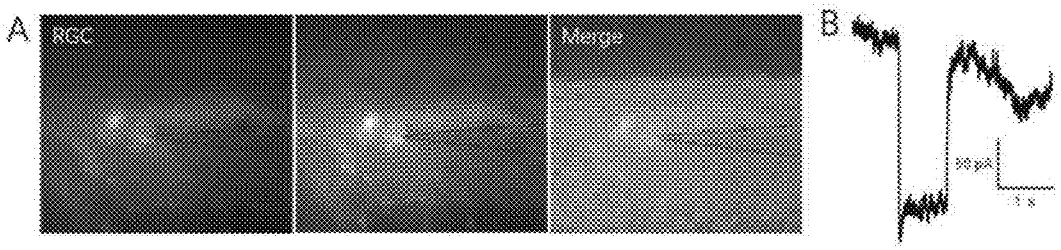
FIG. 4 shows real-time images (A) and photocurrent (B) of ganglion cells in retinal slices of rd1 mice recorded by patch-clamp after treating by intravitreal injection of rAAV2/2-CMV-VR1.0-EGFP.

Example 5: Currents from RGCs Expressing VR1.0-EGFP in the Retina of Rd1 Mice Recorded by Patch-Clamp The rd1 mice treated with intravitreal injection of rAAV2/2-CMV-VR1.0-EGFP in Example 4 were taken and sacrificed, and the retinas were quickly isolated (within 30 minutes) from the extracellular fluid pre-filled with 95% $O_2$+5% $CO_2$. The peripheral tissue of the isolated retinas was carefully cleaned, the retinal ganglion cells (Retina Ganglion Cells, RGCs) layer was placed on Millipore filter paper, and the retinas were cut into 150 μm wide by a manual microtome (Selelting Tissue Slicer, USA). Whole-cell mode patch-clamp recording were performed at room temperature (25° C.) by standard procedures. The extracellular recording solution comprises the following components: 125 mmol/L sodium chloride, 2.5 mmol/L potassium chloride, 1 mmol/L magnesium sulfate, 2 mmol/L calcium chloride, 1.25 mmol/L sodium dihydrogen phosphate, 26 mmol/L sodium bicarbonate, 20 mmol/L glucose; and mixed gas (95% $O_2$+5% $CO_2$) was pre-filled at least 30 minutes before use. The electrode solution comprises the following components: 115 mmol/L cesium methanesulfonate, 20 mmol/L cesium chloride, 2.5 mmol/L magnesium chloride, 0.6 mmol/L ethylene glycol bis(2-aminoethyl ether)tetraacetic acid, 10 mmol/L 4-hydroxyethylpiperazine ethane sulfonic acid, 4 mmol/L adenosine 5'-triphosphate magnesium salt, 0.4 mmol/L guanosine 5'-triphosphate sodium salt, 10 mmol/L phosphocreatine; adjusting the pH to 7.2 by cesium hydroxide. The photostimulation system and patch-clamp device are the same as those in Example 4, but the patch electrodes in this experiment are made of borosilicate glass and pulled to 5-7 MΩ. The results are shown in FIG. 4, FIG. 4A shows the images of retinal sections of rd1 mice treated with rAAV2/2-CMV-VR1.0-EGFP under a fluorescence microscope; FIG. 4B shows the current diagram of RGCs expressing VR1.0-EGFP recorded by whole-cell mode patch-clamp. The retinas of rd1 mice treated with rAAV2/2-CMV-VR1.0-EGFP were recovered the response to light, and could produce light signals.

Example 6: Visual Evoked Potential

Figure 5:
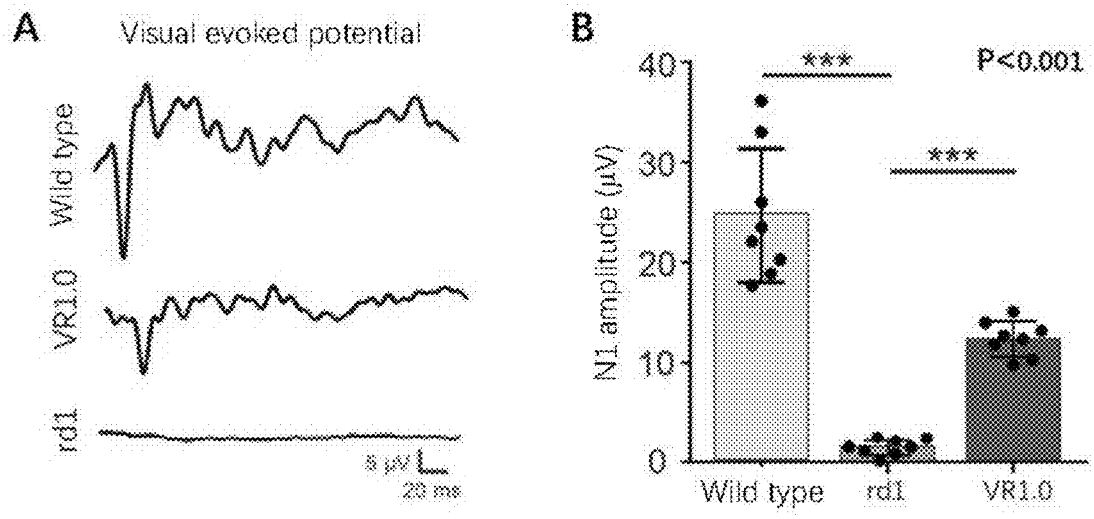
FIG. 5 shows the visual evoked potentials for C57BL/6J, rd1 mice treated with intravitreal injection of rAAV2/2-CMV-VR1.0-EGFP, and rd1 littermate mice without any treatment.

Wild-type C57BL/6J, rd1 mice treated with intravitreal injection of rAAV2/2-CMV-VR1.0-EGFP, and rd1 littermate mice without any treatment were taken to be anesthetized by intraperitoneal injection of a mixture of 100 mg/kg ketamine and 12 mg/kg xylazine. The hair between the two eyes and the two ears of the mice was removed with a hair clipper, and the bregma and the tip of the herringbone suture were fully exposed. The heads of the mice were fixed by a brain stereotaxic device (RWD, Shenzhen, China). 48 hours before the flash visual evoked potential (Flash VEP) experiment, a silver wire electrode with a diameter of 0.25 mm was implanted in the right primary visual cortex (recording electrode, at 3.6 mm away from bregma, 2.3 mm on both sides). Before the experiment, the mice were allowed in dark adaptation for 8 hours, and then the mice were anesthetized by intraperitoneal injection of a mixture of 100 mg/kg ketamine and 12 mg/kg xylazine, and compound tropicamide eye drops (0.5% tropicamide+0.5% phenylephrine hydrochloride) was used for pupil dilation for 5 min. The reference electrode was inserted under the skin between the eyes, and the ground electrode was clipped on the mouse tail. 64 repetitions of light stimulation (2800 μs, blue light, 5.0 cds/m 2) were performed by a flash stimulator (IRC, China, Chongqing). When the band-pass filter is between 3.0 and 70.0 Hz, recording the experimental results with a sampling f of 2000 Hz, generating and recording the data by RetiMINER 4.0 software (IRC, China, Chongqing) to obtain the N1 amplitude data table, and the significance was evaluated by one-way analysis of variance (one-way ANOVA); $P<0.001$, there is a significant difference. The results are shown in FIG. 5, the N1 amplitude of FVEP in wild-type C57BL/6J mice is −24.7±6.7 μV, and that of rd1 mice after intravitreal injection of rAAV2/2-CMV-VR1.0-EGFP is −12.4±1.8 μV, and 1.6±1.0 μV for rd1 mice, n=8. It shows that the visual signal generated in the retina of rd1 mice after intravitreal injection of rAAV2/2-CMV-VR1.0-EGFP is transmitted to the V1 area of the visual cortex.

Example 7: Light-Induced Light/Dark Box Behavior Experiment of Mice

Figure 6:
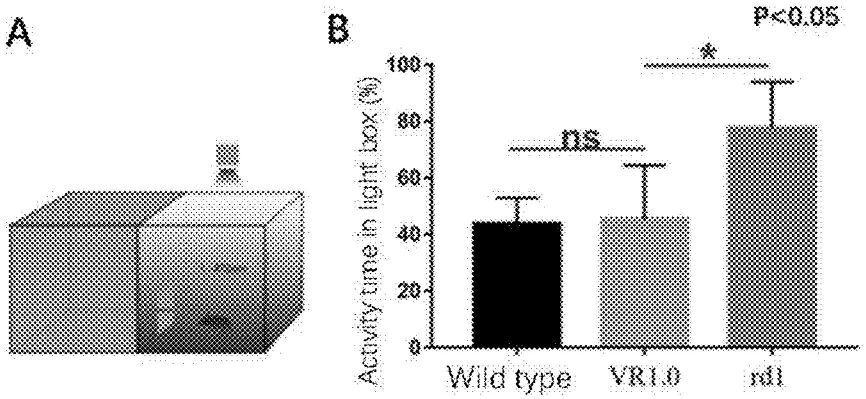
FIG. 6 shows the tendency or escape responses to light in a light/dark box for C57BL/6J, rd1 mice treated with intravitreal injection of rAAV2/2-CMV-VR1.0-EGFP, and rd1 littermate mice without any treatment.

The light/dark box consists of two left and right compartments of the same size (18 cm*20 cm*18 cm), and the two compartments are connected by an arched door (7 cm*5 cm). The light box is equipped with a 470 nm LED light source (Mightex, Canada), and the dark box is wrapped with a black cloth cover. All wild-type C57BL/6J, rd1 mice treated with intravitreal injection of rAAV2/2-CMV-VR1.0-EGFP, and littermate rd1 mice without any treatment were all between 10-12 weeks old. The mice were allowed in dark adaptation for 2 hours before the experiment. All behavioral experiments were performed between 18:00 and 21:00 pm. At the beginning of the experiment, the C57BL/6J, rd1 mice treated with intravitreal injection of rAAV2/2-CMV-VR1.0-EGFP, and littermate rd1 mice were respectively placed in a light box with a blue light (470 nm) intensity of $4.7\times10^{14}$ photons/$cm^2$ s alone. The mouse was allowed to explore freely in the light box, then analyzing the movement of the mouse in the light or dark box based on the position of the mouse's head. The collected data were subsequently imported into Prism 7 (GraphPad Software, La Jolla, CA). The significance was evaluated by one-way ANOVA, and $P<0.05$ was considered significant. The results are shown in FIG. 6; FIG. 6A: schematic pattern of the experiments in a light/dark box; FIG. 6B: statistical histogram of the activity time of the above three groups of mice in a light box. The ratio of activity time in the light box to the total time are as follows: C57BL/6J mice: 40.1%±2.1, n=11; rd1 mice after intravitreal injection of rAAV2/2-CMV-VR1.0-EGFP: 40.8%±3.7, n=19; rd1 mice: 86.1%±4.0, n=13. rd1 mice after intravitreal injection of rAAV2/2-CMV-VR1.0-EGFP have restored the escape response to light, demonstrating that VR1.0 can restore visually guided behavior in rd1 mice with retinal degeneration, and is effective in treating retinal degenerative diseases.

The above examples are preferred embodiments of the present application, but the embodiments of the present application are not limited by the above Examples, and any other changes, modifications, substitutions, combinations, simplifications without departing from the spirit and principle of the application should be equivalent replacement methods, and all of them should fall in the protection scope of the present application.

The invention claimed is:

1. A light-sensitive channel protein VR1.0, wherein the amino acid sequence of the light-sensitive channel protein VR1.0 comprises SEQ ID NO: 1.

2. An encoding gene of a light-sensitive channel protein VR1.0, wherein the nucleotide sequence of the encoding gene by comprises SEQ ID NO: 2.

3. A vector comprising the encoding gene of a light-sensitive channel protein VR1.0, wherein the encoding gene of the light-sensitive channel protein VR1.0 comprises SEQ ID NO: 2.

4. A medicament comprising the light-sensitive channel protein VR1.0 according to claim 1.

5. A medicament comprising the encoding gene of a light-sensitive channel protein VR1.0, wherein the nucleotide sequence of the encoding gene comprises SEQ ID NO: 2.

* * * * *

SEQUENCE LISTING

```
Sequence total quantity: 2
SEQ ID NO: 1            moltype = AA  length = 341
FEATURE                 Location/Qualifiers
REGION                  1..341
                        note = VR1.0
source                  1..341
                        mol_type = protein
                        organism = synthetic construct
SEQUENCE: 1
MRPQILLLLA LLTLGLANGT EGPNFYVPFS NKTGVVRSMG FQLNPEYLNE TILLDDCTPI  60
YLNVGPLWEQ KVARGTQWFG VILSLAFLIY YIWITYKATC GWEELYVCTI EFCKIVIELY  120
FEFSPPAMIY QTNGEVTPWL RYAEWLLTCP VICIHLSNIT GLNDDYSGRT MSLITSDLGG  180
ICMAVTSALS KGWLKWLFFV IGCCYGASTF YHAALIYIES YYTMPHGVCK NMVLAMAAVF  240
FTSWFMFPGL FLAGPEGTNA LSWAGSTIGH TVADLLSKNA WGMIGHFLRL EIHKHIIIHG  300
DVRRPITVNT LGREVTVSCF VDKEEEDEDE RISTKTYANR A                     341

SEQ ID NO: 2            moltype = DNA  length = 1023
FEATURE                 Location/Qualifiers
misc_feature            1..1023
                        note = Encoding gene sequence of VR1.0
source                  1..1023
                        mol_type = other DNA
                        organism = synthetic construct
SEQUENCE: 2
atgcgacccc aaatactcct cttgctggct ttgttgaccc ttggactggc taacggaaca  60
gaaggtccca acttctacgt tcctttcagc aataagacag gcgtagtcag atccatgggc  120
ttccagctca atccggaata cctgaacgaa acaattttgc tggacgactg tacgccaatc  180
tatctgaacg tcggtcccct gtgggagcaa aaggttgccc gaggtacgca atggtttggt  240
gttatcctct cgttggcgtt tctcatctat tatatatgga taacatataa ggcgacttgc  300
ggatgggaag aactgtacgt gtgtacgatc gaattttgta aaattgtaat tgaactctac  360
ttcgagtttt cgcctccggc gatgatatat cagaccaacg gagaggtaac gccctggttg  420
cgatatgctg aatggctctt gacctgccca gtcatttgca tacatttgag taacattaca  480
ggactcaatg acgactattc gggccgaact atgtccctga tcacatccga cctgggaggc  540
atctgcatgg ccgttacttc cgccttgagt aaaggctggt tgaagtggct ctttttcgtg  600
atcggctgtt gttacggtgc tagtacgttt tatcatgcgg cgctcatata tatagaaagt  660
tactacacta tgcctcacgg tgtttgtaaa aacatggtat tggcgatggc agcggtattt  720
tttacaagtt ggttcatgtt tcccggtttg ttcctggcag gccctgaagg aaccaatgca  780
ctgtcgtggg cgggctcgac tatcggtcat accgtggcag atttgctctc caaaaacgcc  840
tggggtatga ttggtcactt cctccgactg gagatacaca aacatataat tattcatggt  900
gatgttcgtc gcccgataac ggttaatacc ttgggacgag aagtcacggt gtcgtgtttt  960
gtcgataaag aagaggagga tgaagacgaa cgtatcagca ctaagaccta cgcgaaccgg  1020
gca                                                                1023
```